United States Patent

Mazza et al.

Patent Number: 5,843,523
Date of Patent: Dec. 1, 1998

[54] ELASTIC BANDAGING MATERIAL

[75] Inventors: Richard J. Mazza, New Hartford; Thomas King, Clinton; Joy Stone, Oriskany Falls, all of N.Y.

[73] Assignee: Tyco Group S.a.r.l., Luxembourg

[21] Appl. No.: 68,345

[22] Filed: May 27, 1993

Related U.S. Application Data

[62] Division of Ser. No. 942,548, Sep. 9, 1992, Pat. No. 5,397,298.

[51] Int. Cl.⁶ .............................. B05D 5/10; A61F 13/00
[52] U.S. Cl. ........................................... 427/208.8; 602/41
[58] Field of Search ................................... 156/289, 315, 156/324; 427/208.8; 602/41, 42, 44, 60, 75–77, 703; 606/214–216, 203; 2/16, 22

[56] References Cited

U.S. PATENT DOCUMENTS

| | | | |
|---|---|---|---|
| 2,415,276 | 2/1947 | Buckley | 427/208.8 |
| 2,487,060 | 11/1949 | Pike | 427/208.8 |
| 2,508,855 | 5/1950 | Brown | 602/903 |
| 3,357,425 | 12/1967 | Morgan | 602/41 |
| 3,475,196 | 10/1969 | Bartell et al. | 427/208.8 |
| 3,618,754 | 11/1971 | Hoey | 428/231 |
| 4,260,659 | 4/1981 | Gobran | 428/217 |
| 4,366,814 | 1/1983 | Riedel | 602/77 |
| 4,379,806 | 4/1983 | Korpman | 428/354 |
| 4,522,870 | 6/1985 | Esmay | 428/252 |
| 4,737,400 | 4/1988 | Edison et al. | 428/230 |

*Primary Examiner*—Daniel Stemmer
*Attorney, Agent, or Firm*—Gene Kartchner; David Warmbold

[57] ABSTRACT

A breathable, comfortable, elastic pressure sensitive, permanent tacky, adhesive bandaging material is disclosed. The material includes a fabric formed of stretch and non-stretch filling and warp yarns which are coated with a release agent, a stiffening agent, and an adhesive material. Both the agents and adhesive material are applied to the backside of the fabric, with a small amount of the release agent being absorbed through the fabric to the face surface thereof. The adhesive material may include a solvent which tends to plasticize the stiffening agent to a small degree when applied thereto. The resulting bandaging material exhibits characteristics of good tearability along with a relatively soft face surface and an improved hand. The material is manufactured by applying the agents and adhesive to the fabric when the fabric is in a relaxed state. When subsequently stretched, the adhesive is pulled into a random, nonuniform and discontinuous layer. The present invention is particularly useful for wrapping a user's limb in a plurality of layers such as is commonly done for protection or support during participation in a strenuous activity such as an athletic event.

4 Claims, 5 Drawing Sheets

ELASTIC BANDAGING MATERIAL

This is a divisional of application Ser. No. 07/942,548 filed on Sep. 9, 1992 now U.S. Pat. No. 5,397,298.

BACKGROUND OF THE INVENTION

1. Field of the Invention

The present invention relates generally to elastic bandaging material. More specifically, the present invention relates to elastic bandaging material having a reduced stiffness and improved hand and softness without a significant reduction in the tearability thereof.

2. Prior Art

In many instances, especially for example during preparation for athletic events, it is common for a person to wrap bandaging material about various joints such as the knee, ankle, elbow, or wrist, in order to reinforce and strengthen the joint against injury during participation in the athletic event. For this purpose, elastic-type wraps or bandaging materials have been used to reinforce the joint by wrapping the material about the joint in a plurality of layers. It has also been preferable in many such situations to use a wrap or bandaging material which is adhesively coated to ensure that the material remains in place during repeated flexing of the joint and movement of clothing or equipment thereover.

Prior art types of bandaging material which include an adhesive coating have often suffered from lack of flexibility and extremely poor breathability. Further, prior art adhesively coated bandaging materials are generally brittle in feel and stiff in hand due to the various coatings (or layers) of agents applied thereto which facilitate their manufacture and use.

For example, Hoey, U.S. Pat. No. 3,618,754, discloses an adhesively coated elastic bandaging material and a method of manufacture thereof. A fabric web is conveyed in a fully stretched condition and an adhesive coating is applied thereto in a high heat environment. By applying the adhesive material to the fabric while in a fully stretched condition, the resulting bandaging material of Hoey tends to have relatively poor breathability when used, due to the contiguous uniform coating of adhesive material thereon which is substantially air impermeable. Further, the high heat environment used in the manufacture of Hoey's bandaging material tends to cause the stretch warp yarns in the fabric thereof to loose a substantial amount of their original elasticity.

Edison et al., U.S. Pat. No. 4,737,400, attempts to solve some of these problems by an alternative method of manufacturing an elastic bandaging material which includes conveying a continuous web of fabric in a substantially relaxed condition to receive an application of adhesive thereon directly subsequent to a preparatory application of steam. The adhesive is applied in a level layer to the entire backside of the relaxed fabric web and a stiffening agent and a release agent are applied to the face side. The resulting bandaging material has a continuous adhesive layer which has a smooth exposed surface and a substantially uniform depth throughout when the material is in its relaxed state. However, when the material is stretched in use, the adhesive layer thereon is pulled into a discontinuous surface which is entirely absent of adhesive in areas, thus allowing breathability of the material when in use. The stiffening agent increases tearability of the material, and the release agent prevents sticking of the adhesive to the top surface of the material when it is formed into a roll for use.

Although the Edison et al. material is a significant improvement over Hoey in its method of producing an elastic, adhesively coated bandaging material, it nevertheless leaves room for improvement.

For example, the Edison et al. bandaging material has a very high cross-sectional profile, due to the weave pattern of the fabric used therein, which tends to generate bulkiness when the material is wrapped in layers upon itself about a person's limb or joint. Further, and more importantly with respect to the present invention, due to the stiffening agent on the face side of the material which assists in increasing the tearability thereof, the material's face side is relatively brittle in feel, having a stiffness that is less than desirable for some uses. For example, the relatively rigid and rough feel of the face side of the Edison et al. material can be somewhat uncomfortable and even develop into a source of irritation to the user during use.

There therefore continues to exist a need in the prior art to develop an elastic, adhesive bandaging material which exhibits the characteristic of good tearability, yet is also significantly softer than the above described prior art material and has an improved hand and comfort in use.

OBJECTS AND SUMMARY OF THE INVENTION

It is an object of the present invention to provide an adhesive coated bandaging material which exhibits the characteristics of good tearability while at the same time has an improved hand and softer face surface than prior art bandaging material.

It is another object of the present invention to provide an adhesive coated bandaging material which is less bulky than prior art bandaging material when wrapped upon itself in layers about a user's limb.

It is further an object of the present invention to provide an adhesive coated bandaging material, including a method of manufacture thereof, which includes the application of a stiffening agent, a release agent and an adhesive to the back side of the fabric in order to form a material having good tearability while at the same time having an improved hand and a soft face surface.

It is also an object of the present invention to form the above bandaging material from an elasticized fabric if desired for particular intended uses.

These and other objects of the present invention are realized in a preferred embodiment thereof, described for purposes of illustration only and not as limitation thereto, which includes a fabric formed of filling yarns interwoven with stretch and non-stretch warp yarns in a "tabby" or "checkered" weave pattern, the filling yarns being either stretch or non-stretch yarns or a combination thereof as desired, and the fabric being coated on its back side with a release agent, a stiffening agent and an adhesive. The method of manufacturing the preferred embodiment of the invention includes conveying a continuous web of the fabric from an unwind stand into a scray. From the scray, the relaxed fabric passes over steam and the material is shrunk. An acrylic stiffening agent is then applied to the back side of the fabric, the material is dried over a series of steam cans to dry the acrylic. The material then runs directly from the steam cans and over a surface roller to a spray booth to apply the release agent. After the material is sprayed it passes over a second set of steam cans and wound up on a core. A layer of adhesive material is applied directly over the agents on the back side of the conveyed relaxed fabric and dried with low heat. The material is then wound into a roll and is slit into a plurality of smaller rolls having the desired roll width for their intended end use.

The adhesive covers a substantial portion of a backside of the fabric when the material is in a relaxed condition and forms a smooth exposed surface at a substantially uniform depth throughout. However, when the fabric is stretched, the adhesive is drawn into a randomly discontinuous pattern of uneven depth, thus increasing breathability of the material. The weave of the material and the adhesive layer are specifically chosen and formed to minimize the cross-sectional profile of the material both in its stretched and non-stretched states. Also, the modulous of elasticity of the adhesive is specifically chosen to be less than the modulous of elasticity of the fabric in order to ensure overstretching of the adhesive during use to generate the random open adhesive pattern on the backside of the material which increase its breathability. The fabric preferably contains absorbent yarns which will transport a small portion of the release agent through capillary action to the face side thereof in order to inhibit separation of the adhesive from the back side of the fabric when being unwound from the roll.

DETAILED DESCRIPTION

As shown in the exemplary drawings, for the purposes of illustration only and not by way of limitation, a preferred embodiment of an elastic adhesive bandaging material made in accordance with the principles of the present invention is provided for layered wrapping of various body parts with good tearability, and improved hand and softness over prior art bandages.

Figure 1:
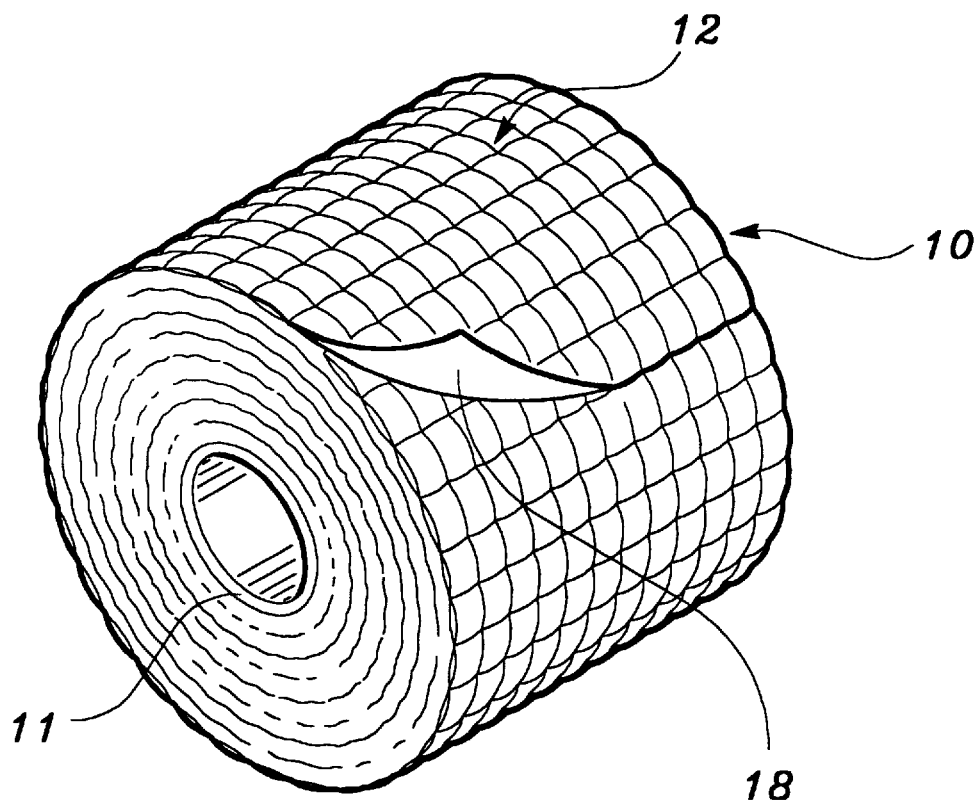
FIG. 1 is a perspective view of a roll of bandaging material formed in accordance with the principles of the present invention.

More specifically, as shown in FIG. 1, the bandaging material 10 of the present invention is shown rolled on a cardboard core 11 in its relaxed state, and has an adhesive coating 18 on its back surface.

Figure 2:
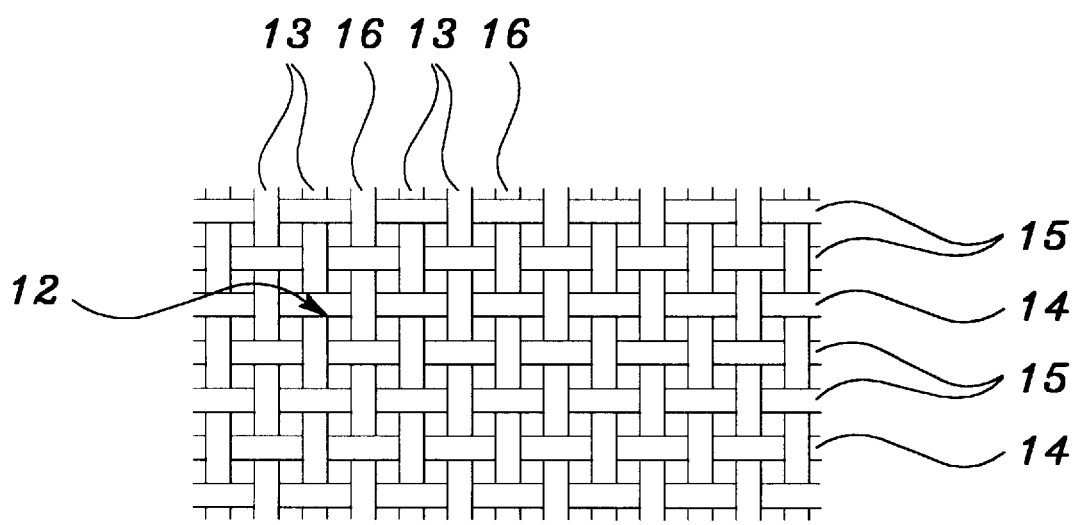
FIG. 2 is an enlarged plan view of a preferred embodiment of the fabric formed in accordance with the principles of the present invention showing the particular weave pattern thereof.

As best shown in FIG. 2, the material 10 is made from a fabric 12 which may be formed by essentially non-stretched filling yarns 13 interwoven with warp yarns consisting of stretch yarns 14 interspersed with essentially non-stretch yarns 15 in a "tabby" or "checkered" weave pattern. Alternatively, the fabric 12 may be formed with non-stretch filling yarns 13 and stretch filling yarns 16 interwoven with the stretch and non-stretch warp yarns 14 and 15 respectively in a similar weaving pattern should it be desired to have two dimensional stretchability of the finished bandaging material 10.

It is desirable, although not required, that for many aspects of the present invention, the weave of the fabric 12 be of a pattern which forms a very low cross-sectional profile when it is in the relaxed state, and forms a cross-sectional profile which is as near as possible to being completely flat when in the stretched state. The choice of a "tabby" or "checkered" weave for the fabric 12 of the present invention would specifically avoid a high cross-sectional profile such as is generated by prior art bandaging material. The desired "tabby" weave pattern of the present invention causes the material 10 to "bunch" together in a random, non-uniform manner when relaxed, and avoids the high profile which is generated in the prior art, specifically for example, in the Edison et al. bandaging material described in U.S. Pat. No. 4,737,400 discussed above, which forms a corrugated and undulating surface when in its relaxed state. This aspect of the present invention is more completely disclosed in co-pending U.S. patent application Ser. No. 892,862, filed Jun. 3, 1992, assigned to the assignee of the present application and incorporated herein by reference.

Even though a "tabby" or "checkered" weave pattern has been described as a specific preferred embodiment of the present invention, any fabric 12 may be used to form the bandaging material 10. Nevertheless, it is desirable to choose a fabric 12 which significantly inhibits the generation of any uniform corrugation or undulating surface pattern when in the relaxed state, and instead forces a random "bunched" pattern as a result of the elastic contraction of the stretch yarns 14 and 16 therein as more fully described and explained in the above-mentioned co-pending U.S. patent application. It is also desirable that the fabric 12 in its relaxed state form a "bunched" back surface which confines application of the adhesive material 18 to only a portion of the total back surface area which is exposed when the fabric 12 is stretching.

The preferred fabric 12 used in the described embodiment of the present invention is fabricated of essentially non-stretch yarns such as cotton, and stretchable yarns consisting of core spun, DUPONT LYCRA SPANDEX filaments wrapped with fibers of cotton and polyester.

Figure 3:
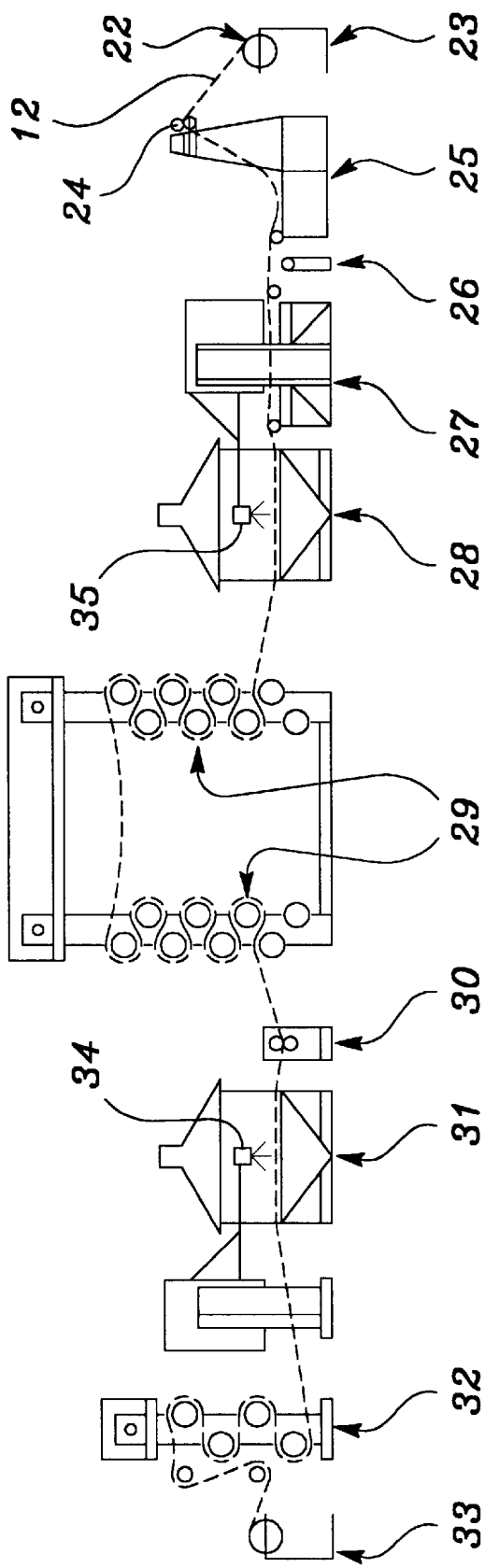
FIG. 3 is a schematic view showing the conveying of the fabric in a relaxed condition through a scray, proceeding to the stiffening agent spray booth and being dried on a set of steam cans, then being passed through the release agent spray booth and dried on a second set of steam cans. The material is then rolled up on a rewind stand.

Manufacture of the preferred embodiment of the bandaging material of the present invention is as follows, starting with the step of steam application to the fabric 12. Referring to FIG. 3, a roll 22 of fabric 12 is mounted on a roll stand 23 which is unwound by the pull rolls 24 and placed into the scray 25. The fabric 12 is pulled over the steam box 26 by the conveyor 103. The steam spray is spread so that steam is directed against the entire surface of the fabric 12. The purpose of the steam application is to exfoliate and spread and loosen the cotton filling yarns 13 and cotton warp yarns 15, and to permit the core filaments of the stretch filler yarns 16 and stretch warp yarns 14 to contract to the maximum extent possible. The steaming step also opens the pores and enhances the breathability of the fabric 12, especially when the fabric 12 is later stretched, and increases the capability of the fabric 12 to be repeatedly stretched for extended periods of time during use, while at the same time retain its ability to return to substantially its original non-stretch length after stretching.

After steam has been applied to the relaxed fabric by steam box 26, the fabric is further conveyed in a relaxed condition through the stiffening agent spray booth 28 where it is sprayed, in the preferred embodiment with acrylic. After the fabric 12 passes the stiffening agent spray booth 28, it is conveyed over a series of steam cans 29 to dry the acrylic. It should be understood that drying of the fabric 12 can be performed in several other ways well known in the art, so long as the fabric 12 is not stretched during drying, nor the temperature of the fabric 12 raised sufficiently to reduce the elastic strength of the stretch yarns 14 or 16. In the case of the presently described preferred embodiment, it is preferred that the temperature 12 of the fabric remain below approximately 235° F. By keeping the fabric 12 relaxed throughout the entire steam application process and by avoiding heating the fabric 12 to above approximately 235° F., the fabric 12 will retain a maximum amount of its elastic strength.

The fabric 12 exits the steam cans 29 and passes through pull rollers 30 before entering the release agent spray booth 31. After fabric 12 has been sprayed with release agent the material is dried by a set of steam cans 32 and rolled up on the rewind stand 33. Although being shown as a single processing operation, it should be noted that combination of the release agent application step with the steam and acrylic application steps is not mandatory.

A spray head 35 is mounted above the fabric 12 in the acrylic spray booth 28 and is arranged to spray the entire backside of the fabric 12 with a fluid coating containing an acrylic agent 21 which will stiffen the fabric 12 in order to make it easy to laterally tear the fabric 12 by hand, and to reduce the fraying of the edges of the fabric 12 when manually torn. The stiffening agent 21 prevents unraveling of the yarns during tearing, resist twisting of the yarns, gives more dimensional stability to the yarns, and significantly effects the "hand" characteristics of the fabric 12.

A second spray head 34 is mounted in the release spray booth 31 above the fabric 12 and is arranged to spray the entire backside of the fabric 12 with a fluid coating containing a release agent 20. The preferred released agent 20 is a water-borne silicone polymer. The spray head 34 is designed to allow the release agent 20 to be sprayed across substantially the entire back side of the fabric 12. Due to the absorptive nature of the fabric 12, the release agent 20 will be absorbed a substantial distance through the thickness of the fabric 12, even possibly clear through to the face side of the fabric 12 at limited locations.

The release agent 20 and the stiffening agent 21 are preferably sprayed in a latex form for ease of application to the fabric 12. It should be understood however that the agents could be applied to the fabric by means other the spray heads 34 and 35. Further, it should be understood that it is within the scope of the present invention, if desired, to apply both the release agent 20 and the stiffening agent 21 in combination through a single spray head. Also, the spray head may be cam driven so as to swing from side to side in a precisely timed manner to cause the entire back side of the fabric 12 to be covered with an equal amount of the spray fluid.

After the agents 20 and 21 have been sprayed on the backside of the fabric 12, the relaxed fabric 12 is dried on steam cans 29 and 32, respectively. Then the dried fabric is rolled up in a completely relaxed condition on rewind stand 33 in preparation for the next step of the manufacturing process which is the application of adhesive over the stiffening and release agents.

Figure 4:
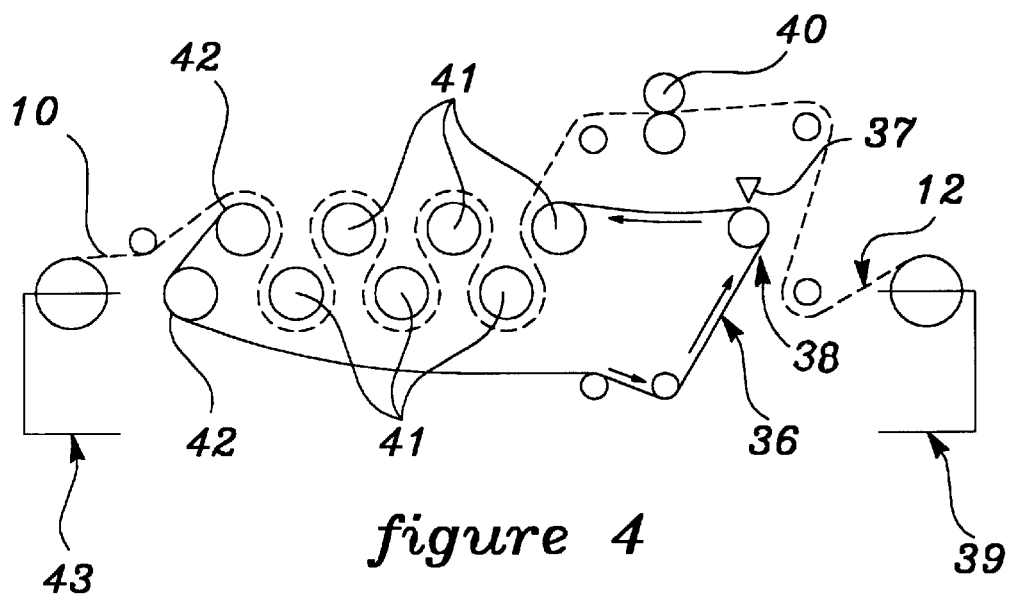
FIG. 4 is a schematic view showing the conveying of the fabric in a relaxed condition through and adhesive application.

FIG. 4 shows the adhesive application step in the manufacturing process. However, as previously explained with regard to the option of making contiguous the process steps shown in FIG. 3, the processing step shown in FIG. 4 can also be made contiguous with the immediately preceding and/or immediately succeeding manufacturing steps. However, for purposes of illustration, FIG. 4 shows a conveyor belt 36 which has a release coated surface and continuously travels in the direction shown. Blade 37 is mounted over a coating roller 38 in a conventional manner such that the blade 37 can be accurately adjusted to provide a desired spacing above the conveyor belt 36.

Adhesive material 18 is continuously applied to the conveyor belt 36 from a trough (not shown) immediately upstream of the blade 37. The conveyor belt 36 carries the adhesive material 18 against and under the blade 37, which causes the adhesive material 18 to be coated onto the conveyor belt 36 in a level layer having a uniformed depth. The fabric 12, having been previously steamed and coated with release and stiffening agents 20 and 21, is unrolled from unwind stand 39 by means of pull rollers 40 in a completely relaxed condition and dropped onto the conveyor belt 36 at a position immediately downstream of the blade 37. Thus, the backside of the fabric 12 is brought into contact with the adhesive material 18. The fabric 12 and adhesive material 18, in engagement with each other, are then conveyed over and around a series of steam cans 41 and chilled cans 42 in order to cause the adhesive material 18 to permanently adhere to the backside of the fabric 12.

It is important to note that the adhesive material 18 is applied to the backside of the fabric by a very light pressure contact. The conveyor belt 36 is kept only sufficiently taut to prevent slippage of the rollers so that the conveyor belt 111 can gently urge the layer of adhesive material 18 against the back side of the fabric 12 and not up into the interstices thereof to any significant extent. By this method, the adhesive material 18 remains a generally smooth even layer after applied to the backside of the fabric 12.

The preferred adhesive material 18 used in the described process of the present invention is a pressure sensitive, permanently tacky adhesive material containing primarily rubber with various other constituents which increase the tactifying and anti-oxidizing properties thereof. The adhesive material 18 preferably has a high viscosity and a high solids content and is dissolved in a well known solvent which will react with the stiffening agent 21 to plasticize the stiffening agent 21 a predetermined amount, thus slightly softening some of the stiffening agent 21 in order to improve the softness and "hand" of the resulting bandaging material 10, without significantly reducing its tearability. If desired, for anticipated medical uses of the present invention, an adhesive material 18 may be chosen which is hypoallergenic. Also, if desired, the adhesive material 18 may be applied to the backside of the fabric by a different well known process such as by spraying.

After the fabric 12 passes beyond the chilled cans 42, it is peeled away from the release coated conveyor belt 36 by the wind up stand 43. At this point, the application steps of the manufacturing process are complete and the fabric 12 has been effectively processed into bandaging material 10. However, when rolled up on wind up stand 43, the fabric's adhesively coated backside is oriented outwardly, and therefor must be rewound. Since the adhesive material 18 is now applied to the fabric 12 and the adhesive bandaging material 10 is completely formed, it is no longer necessary to maintain the bandaging material 10 in a completely relaxed condition.

Figure 5:
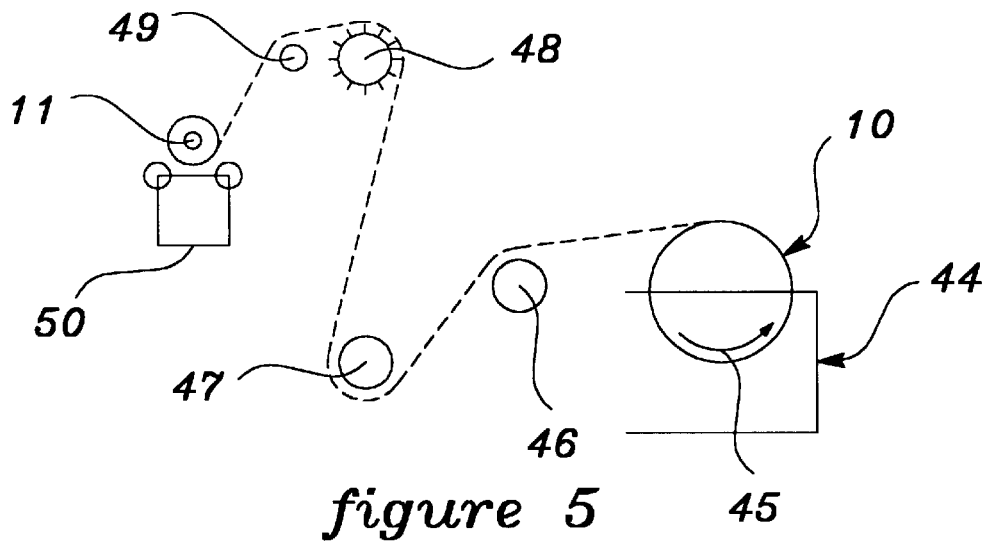
FIG. 5 is a schematic view showing the conveying of the fabric in a relaxed condition through a rewinding step of the preferred manufacturing process of the present invention.

Therefore, as shown in FIG. 5, the next step of the process includes tensioned rewinding of the bandaging material 10 onto a core 11. First, the material 10 is unrolled from a stand 44 in the direction shown by arrow 45 and passes over non-driven bow rollers 46 and 47 which laterally spread the bandaging material 10. The spread bandaging material 10 next proceeds to a driven spike roller 48 which is pulling the material 10 from the stand 44. The bandaging material 10 then proceeds to another driven roller 49, and on to a roll stand 50 which rolls up material 10 directly onto the core 11.

Figure 6:
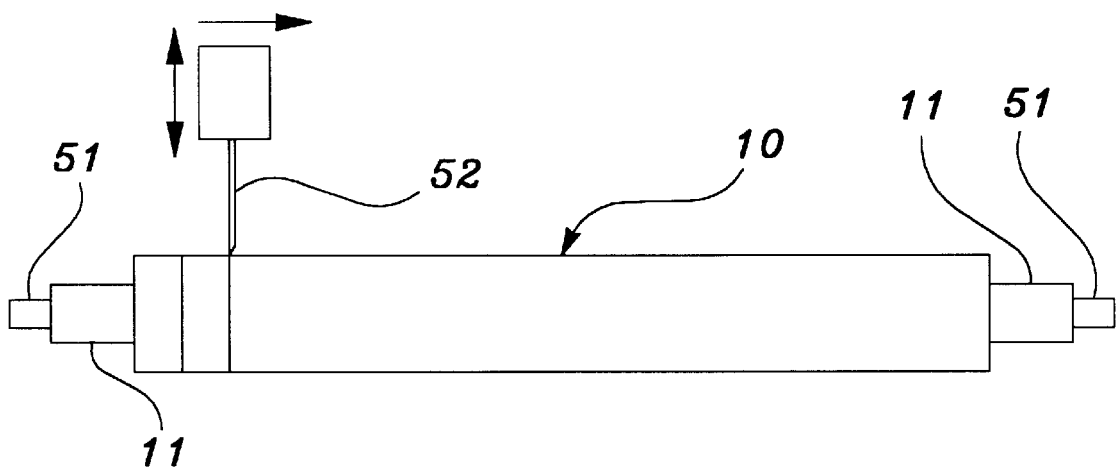
FIG. 6 is a top view showing the slitting of a roll of the bandaging material into a plurality of rolls of desired width.

As shown in FIG. 6, the core 11 is placed onto a steel arbor 51 and rotated past a multidirectional movable blade 52 which cuts the bandaging material 10 and core 11 into a number of more narrow rolls having a desired width. The bandaging material 10 is then ready for packaging to complete the manufacturing process.

Figure 7:
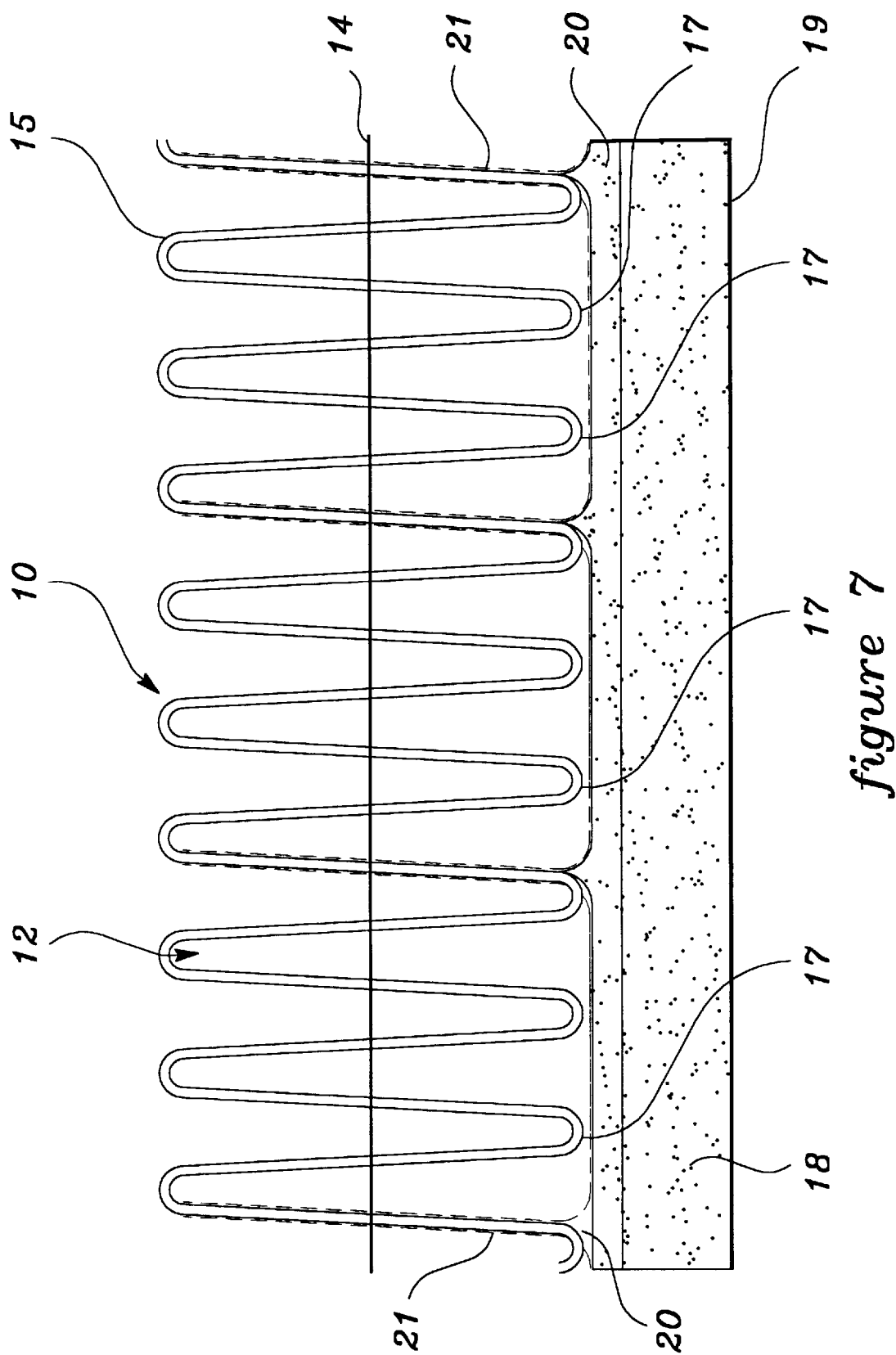
FIG. 7 is a cross-sectional view of the fabric formed in accordance with the principles of the present invention shown in its relaxed state; and, FIG. 8 is a cross-sectional view of the bandaging material formed in accordance with the principles of the present invention similar to the view shown in FIG. 7, except that the material is shown in its stretched state.

Returning now to the structural elements of the bandaging material 10, FIG. 7 shows a cross-section of the bandaging material 10 in its relaxed state. The stretch warp yarn 14 is relaxed and in a generally flat planar orientation within the fabric 12. The non-stretch warp yarn 15 is thus randomly, yet tightly, bunched together in order to accommodate the extra length thereof. The non-stretch warp yarn 15 surfaces on the back side of the fabric 12 at several random locations 17 therealong, which are below the plane in which the stretch warp yarn 14 is located. The release agent 20 forms a thin layer on the back side of the fabric 12 as has been explained above, and also absorbs through a portion of the thickness of the fabric 12, to even extend to the face surface of the fabric 12 in limited locations. The stiffening agent 21 also forms a thin layer on the back surface of the fabric 12.

The adhesive material 18 preferably forms a smooth flat exposed surface 19 over a uniform depth when the bandaging material 10 is in its relaxed state. The adhesive material 18 is attached to the relaxed fabric 12 only at the backside thereof and does not extend upwardly to any significant extent into the interstices of the fabric, and specifically does not extend upward to coat the stretch warp yarn 14. This is significant because of its overall effect on the resulting random discontinuous positioning of the adhesive material 18 on the back side of the fabric 12 after it has been drawn into a stretched state for use.

Due to the limited, random extension of release agent 20 up to the face side of the fabric 12 through absorption during the application process thereof, rolling of the adhesive bandaging material 10 into rolls for use does not cause the adhesive material 18 to significantly stick to the face surface of the fabric 12.

Figure 8:
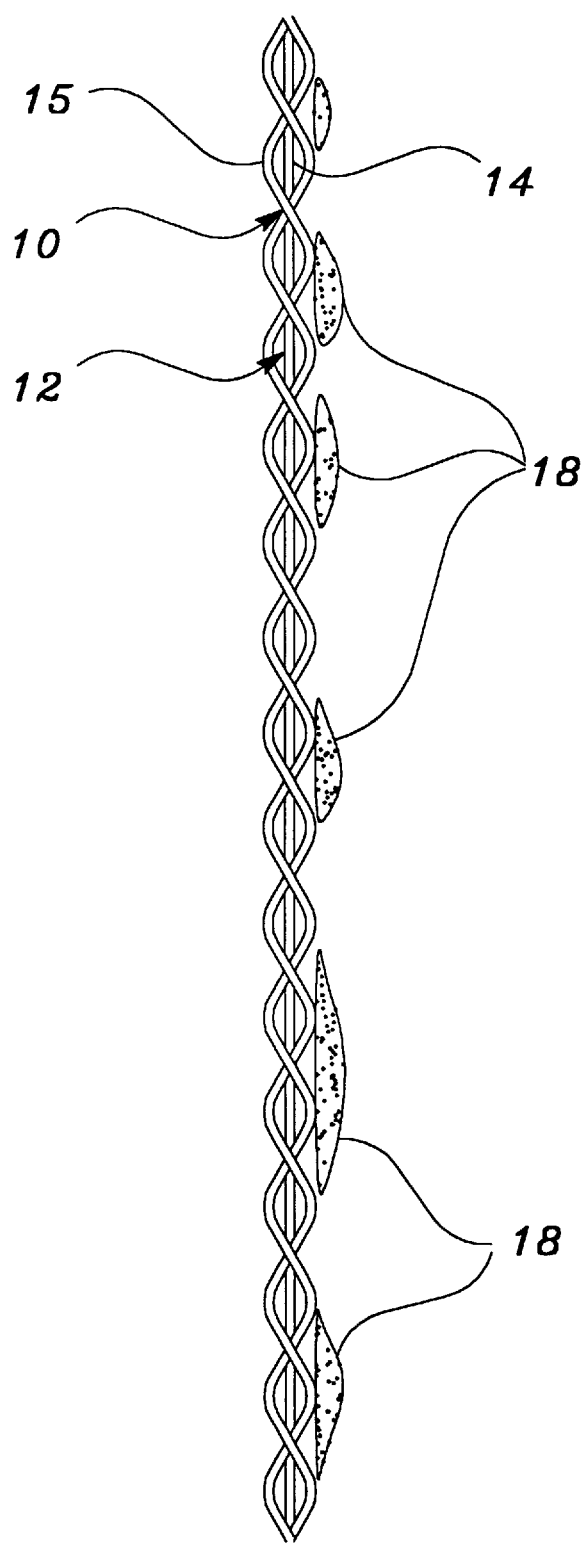

As shown in FIG. 8, when the fabric 12 is in its stretched state, the stretch warp yarn 14 remains planar and generally centered within the fabric. The non-stretch warp yarn 15 however has been drawn out of its "bunched" position to an extended orientation. The adhesive material 18 remains bonded only to portions of the back side which were presented for its attachment when in the relaxed state, which results in the formation of a completely random, non-uniform, discontinuous layer of varying depth on the back side of the fabric 12 when stretched.

Since the fabric of the present invention in its stretched state randomly stretches and separates the adhesive material 18, the depth of the adhesive material 18 at almost all locations is less than the depth thereof when the fabric 12 was in its relaxed state. This is very different from the prior art adhesive of Edison et al. in which a majority of the adhesive layer maintains its original depth after stretching, and is located in a fairly ordered pattern in between large strip shaped areas of the back side of the fabric which are completely absent of adhesive materials, resulting in a significantly elevated cross-sectional profile.

The random and tight "bunching" of the non-stretch warp yarns 15 of the present invention, along with the placement of the stretch warp yarns 14 at a central plane within the cross-section of the fabric 12 to avoid contact of the adhesive material 18 therewith, and the general overall reduction in depth of the adhesive material 18 when the fabric is drawn to its stretched state, all contribute to the overall lower cross-sectional profile of the bandaging material 10 of the present invention than the prior art material such as shown by Edison et al.

The overall reduction in depth and random positioning of the adhesive material 18 in its stretched state is substantially due to the relative difference in the elasticity of the material 10 (at least 50%, and preferably 100%) and the elasticity of the adhesive material 18 (less than 50%).

Due to the discontinuity and the great variance in the depth of the layer of adhesive material 18 when the fabric 12 is in its stretched stated, and due to the overall low cross-sectional profile of the fabric, the bandaging material 10 of the present invention has extremely good breathability, even when repeatedly wrapped upon itself during use.

As mentioned above, the bandaging material 10 of the present invention may be formed of a fabric which also includes stretchable filling yarn 16 whenever it may be desired to have multidirectional stretchability of the bandaging material 10. The stretch filling yarn 16 is preferably positioned generally planar within the fabric 12 at a central cross-sectional location similar to the stretch warp yarns 14, and performs in generally the same manner giving the fabrics similar characteristics in the direction of the fill yarns as in the direction of the warp yarns.

It will be apparent from the foregoing that, while a particular embodiment of the present invention has been illustrated and described, various modifications can be made thereto without departing from the spirit and scope of the invention. Accordingly, it is not intended that the invention be limited, except as by the appended claims.

We claim:

1. A method of manufacturing an adhesive bandaging material comprising the steps of:

forming a fabric having a back side and a face side;

applying a release agent to the back side of the fabric; and, applying an adhesive material to the release agent.

2. A method according to claim 1 wherein the fabric is stretchable between a relaxed state and a stretched state, and said step of applying an adhesive material further includes applying an adhesive material in a generally uniform layer on the release agent when the fabric is in its relaxed state.

3. A method according to claim 1 wherein said fabric is formed of a porous and absorptive fabric and said step of applying a release agent further includes applying a release agent to the back side of the fabric such that a portion of the release agent is absorbed through the fabric to the face side thereof.

4. A method according to claim 1 wherein said step of forming a fabric includes forming a fabric having an elasticity of at least 50% and said step of applying an adhesive material to the fabric further includes applying an adhesive material having an elasticity of less than 50%.

* * * * *